United States Patent
Schwab

(10) Patent No.: US 10,302,538 B2
(45) Date of Patent: May 28, 2019

(54) MEASURING APPARATUS WITH REMOTE CONTROL

(71) Applicant: ROSENBERGER HOCHFREQUENZTECHNIK GMBH & CO. KG, Fridolfing (DE)

(72) Inventor: Martin Schwab, Geretsried-Gelting (DE)

(73) Assignee: ROSENBERGER HOCHFREQUENZTECHNIK GMBH & CO. KG, Fridolfing (DE)

( * ) Notice: Subject to any disclaimer, the term of this patent is extended or adjusted under 35 U.S.C. 154(b) by 270 days.

(21) Appl. No.: 14/911,551

(22) PCT Filed: Aug. 5, 2014

(86) PCT No.: PCT/EP2014/066862
§ 371 (c)(1),
(2) Date: Feb. 11, 2016

(87) PCT Pub. No.: WO2015/022241
PCT Pub. Date: Feb. 19, 2015

(65) Prior Publication Data
US 2016/0187243 A1    Jun. 30, 2016

(30) Foreign Application Priority Data

Aug. 12, 2013 (DE) .................... 10 2013 215 932

(51) Int. Cl.
*G01N 3/30* (2006.01)
*G01M 7/08* (2006.01)

(52) U.S. Cl.
CPC ................ *G01N 3/30* (2013.01); *G01M 7/08* (2013.01)

(58) Field of Classification Search
CPC .................................. G01N 3/30; G01M 7/08
See application file for complete search history.

(56) References Cited

U.S. PATENT DOCUMENTS

| 4,422,320 A | * | 12/1983 | Moorby | .................. G01N 3/30 73/12.09 |
| 5,048,320 A | * | 9/1991 | Mitsuhashi | ............. G01M 7/08 73/12.09 |

(Continued)

FOREIGN PATENT DOCUMENTS

| AU | 2012254886 | 12/2012 |
| CN | 1123748 A | 6/1996 |

(Continued)

OTHER PUBLICATIONS

International Preliminary Report on Patentability for parent application PCT/EP2014/066862, translation provided.

(Continued)

*Primary Examiner* — David Z Huang
(74) *Attorney, Agent, or Firm* — Hassan Abbas Shakir; Shakir Law PLLC

(57) ABSTRACT

A test system includes a measuring apparatus for measuring a property of a device under test and a test hammer for carrying out a strike on a section of the device. The test hammer includes a motion sensor and a transmission module for transmitting a signal if the motion sensor detects the start of the strike, and/or for transmitting a signal if an impact is detected. Further, a test signal generating unit generates a test signal, a test signal output unit outputs the test signal to the device under test, a measuring signal receiving unit receives a measuring signal produced in response to the output of the test signal, an analyzing unit determines a quantity of a component of the measuring signal, a transmission module receives a control signal from an external source, and a real-time controller switches from the energy-saving mode.

18 Claims, 4 Drawing Sheets

(56) References Cited

U.S. PATENT DOCUMENTS

| | | | |
|---|---|---|---|
| 6,748,791 B1 | 6/2004 | Georgeson et al. | |
| 7,146,846 B2 | 12/2006 | Mahaffey et al. | |
| 7,735,351 B2 | 6/2010 | Profit | |
| 2001/0039468 A1* | 11/2001 | Seidl | B60R 21/013 701/45 |
| 2004/0220776 A1 | 11/2004 | Kato | |
| 2009/0095050 A1 | 4/2009 | Profit | |
| 2011/0224923 A1 | 9/2011 | Blair | |
| 2013/0167615 A1* | 7/2013 | Phillips | G01M 99/007 73/12.01 |
| 2013/0224923 A1 | 8/2013 | Mouli | |

FOREIGN PATENT DOCUMENTS

| | | |
|---|---|---|
| CN | 2804872 Y | 8/2006 |
| CN | 2847300 Y | 12/2006 |
| CN | 101828238 A | 9/2010 |
| DE | 10018651 A1 | 12/2001 |
| DE | 102004004891 A1 | 8/2004 |
| EP | 0351430 A1 | 1/1990 |
| JP | 2000206020 | 7/2000 |

OTHER PUBLICATIONS

Office Action in corresponding application CN 201480044402 dated Sep. 5, 2017 by the Chinese State Intellectual Property Office.

Office Action dated Apr. 14, 2014 by the German Patent Office in application DE 10 2013 215 932.3, partial machine translation provided.

Written Opinion of the International Search Authority, International Search Report, Translation of the ISR for application WO2015022241.

Office Action dated Nov. 16, 2018 by the European Patent Office in related European patent application 14 748 205.3 partial machine translation provided.

Office Action dated Mar. 8, 2018 by the Chinese State Intellectual Property Office in related Chinese Patent Application No. 201480044402.x, partial machines translation provided.

* cited by examiner

MEASURING APPARATUS WITH REMOTE CONTROL

BACKGROUND OF THE INVENTION

1. Field of the Invention

The present invention relates to measuring systems for high-frequency communication systems, specifically for measuring apparatus for measuring passive intermodulation.

2. Discussion of the Related Art

The quality of a connection between a permanently installed transceiver device (BTS, Base Transceiver Station) and a terminal device (UE, User Equipment) plays an essential role in today's mobile networks. Due to the high generated power in the BTS on the one hand and the necessary sensitivity of the receivers of the BTS and the UE on the other hand, interference in the transmission path can substantially influence the sensitivity of the receivers and therefore the quality of the connection.

Intermodulation is a determining effect causing interference in the transmission path. Two transmit signals, for example, with two different carrier frequencies which are generated at high power in a BTS generate interference due to intermodulation at points with non-linear transmission behavior (often referred to simply as "non-linearities"), the frequencies of said interference being sums and differences of integral multiples of the frequencies of the transmit signals. A part of this interference can be in the receive band of the BTS and thus adversely affect the quality of the communication. If this interference is generated on passive elements, this is referred to as passive intermodulation (PIM).

FIG. 5 is a schematic representation showing a transmission path from a BTS to an antenna. The BTS 10 is connected via a first filter 11 and a second filter 12 to the antenna 13. The BTS 10, the filters 11 and 12 and the antenna 13 are interconnected via high-frequency cables 14, 15 and 16 which are connected via high-frequency connectors 17 to 22 to the respective elements. PIM can occur in all components 11 to 22 of the transmission path. For example, corrosion in plug-in connectors, oxide layers on contacts and metal-to-metal transitions, contamination in materials and inadequately attached plug-in connections can cause PIM.

PIM measurements are carried out in order to ensure and verify the quality of the transmission device. Since PIM occurs particularly at high powers, it is normally measured with the application of high transmit power, e.g. 2*20 W.

FIG. 6 is a block diagram showing the structure of a known PIM test apparatus (PIM analyzer). It consists of a control unit 151 and a signal unit 161. In the signal unit 161 two high-frequency signals with suitable different frequencies are generated in two signal generators 113 and are amplified in two power amplifiers 114. The two transmit signals are combined in a filter 115 and are fed to the device under test (DUT) 130. The PIM occurring in the DUT is selected in the filter 115 and detected and measured in a measuring receiver 116. The control, the evaluation of the measurement results and their presentation are performed in the control unit 151 which contains a computer 102, for example a standard PC or a microcontroller (μC), and a display 101 such as, for example, a monitor.

A PIM test apparatus, the structure of which is similar to that described above, is disclosed in AU 2012 254 886 A1.

In the example shown in FIG. 5, the entire transmission path between the BTS 10 and the antenna 13 forms the device under test (DUT). Instead of the BTS 10, the PIM test apparatus is therefore connected via the high-frequency connector 17 to the high-frequency cable 14 for the measurement.

In order to stimulate and localize interference which is caused, for example, by inadequately attached connectors, oxidized contacts and contamination, the elements in the transmission path are often mechanically stressed, for example by tapping on plug-in contacts, as a result of which mechanical vibrations are caused. The resulting interference is continuously measured and displayed. If the PIM increases significantly during tapping on one point, this is a sign that this point forms a point of interference in the transmission path.

The high power consumption, particularly of the power amplifiers, and the applied measuring method in which the power amplifiers are continuously in operation while the individual contact points are successively subjected to tapping result in a high total energy requirement.

Easy-to-handle, lightweight and portable measuring apparatus are necessary, particularly for checking transmission paths with restricted access, as is the case on antenna masts or in ceiling installations in buildings. However, only relatively heavy measuring apparatus have hitherto been available in which, on the one hand, due to the high total energy requirement, large batteries or accumulators are used, but, on the other hand, also due to the high power consumption and the resulting power dissipation, large and heavy heat sinks are fitted to remove the waste heat.

The object of the present invention consists in considerably reducing the power consumption of PIM test apparatus, reducing their weight and simplifying their operation.

SUMMARY OF THE INVENTION

According to the present invention, components of the measuring apparatus which have a high power consumption can be switched off in a permanent condition and can be switched on by means of remote control only when the motion sensor in the test hammer sends a control signal to the measuring apparatus to switch on these components. The power consumption of the measuring apparatus can thereby be reduced and the service life increased. Due to the reduced power consumption, smaller batteries and smaller can be used, as a result of which the weight of the apparatus can be reduced. Furthermore, the operation of the measuring apparatus is simplified. The result of the measurement is preferably displayed directly on the test hammer.

BRIEF DESCRIPTION OF THE FIGURES

Further features and useful aspects of the invention can be found in the description of example embodiments with reference to the attached drawings.

DETAILED DESCRIPTION OF THE INVENTION

An embodiment of the present invention is described in detail below with reference to the attached figures.

Figure 1:
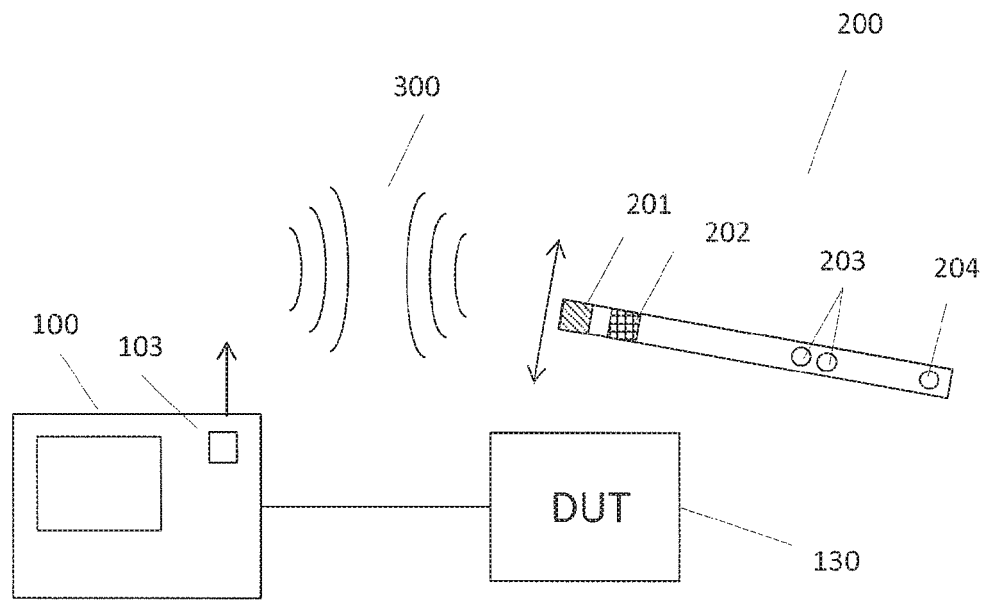
FIG. 1 is a schematic representation showing a test system according to one embodiment of the present invention.
Figure 5:
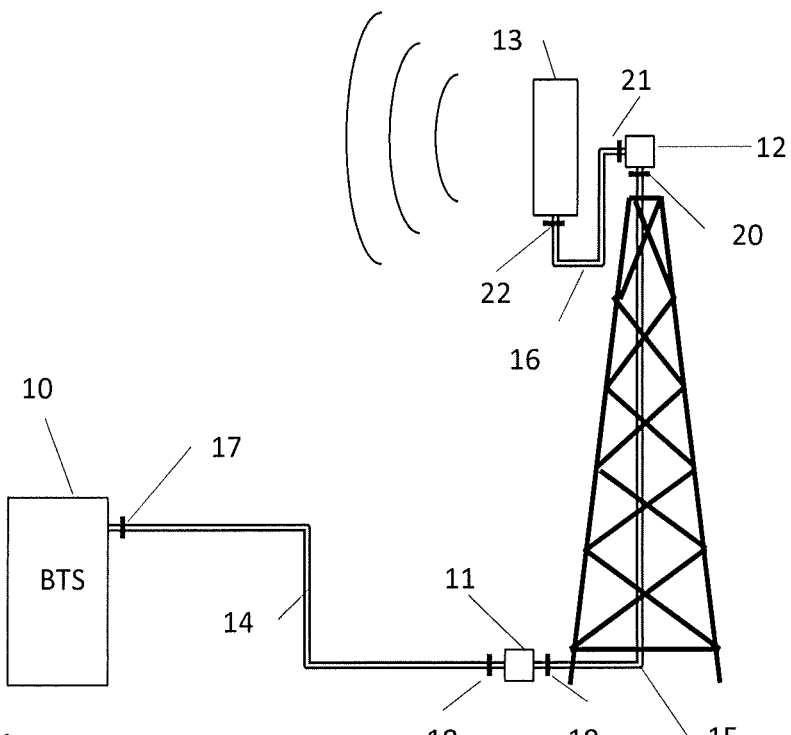
FIG. 5 is a schematic representation showing a transmission path from a BTS to an antenna.
Figure 6:
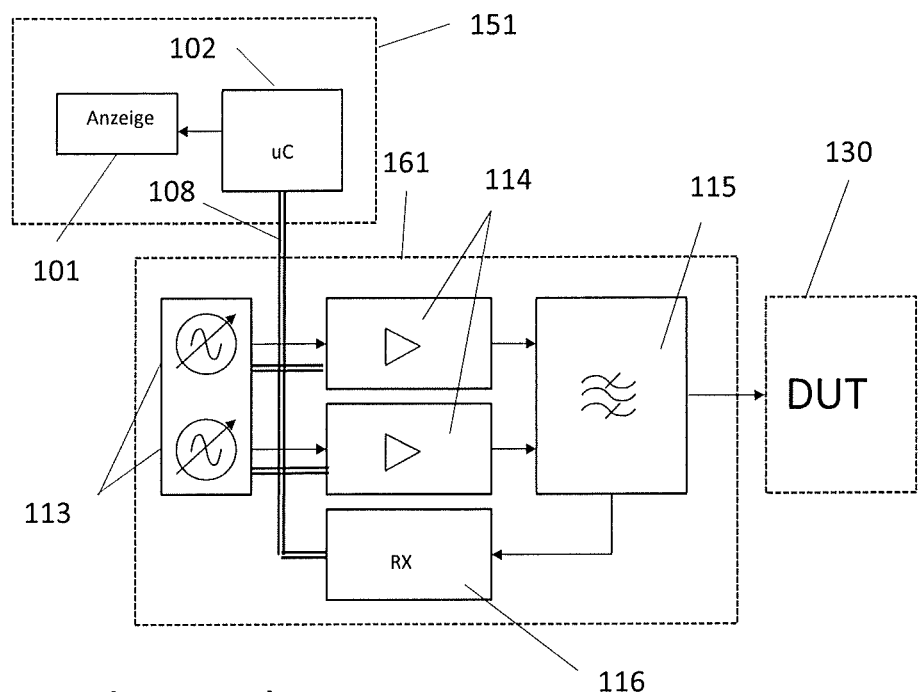
FIG. 6 is a block diagram showing the design of a known PIM test apparatus.

FIG. 1 is a schematic representation showing a test system according to one embodiment of the present invention. A measuring apparatus 100 which is designed as a PIM analyzer is connected to the device under test (DUT) 130. The DUT may, for example, be a transmission path between a BTS 10 and an antenna 13, as shown in FIG. 5 and described in the introduction to the description. In this case, the measuring apparatus 100 is connected, for example, via the high-frequency connector 17 to the high-frequency cable 14.

Figure 2:
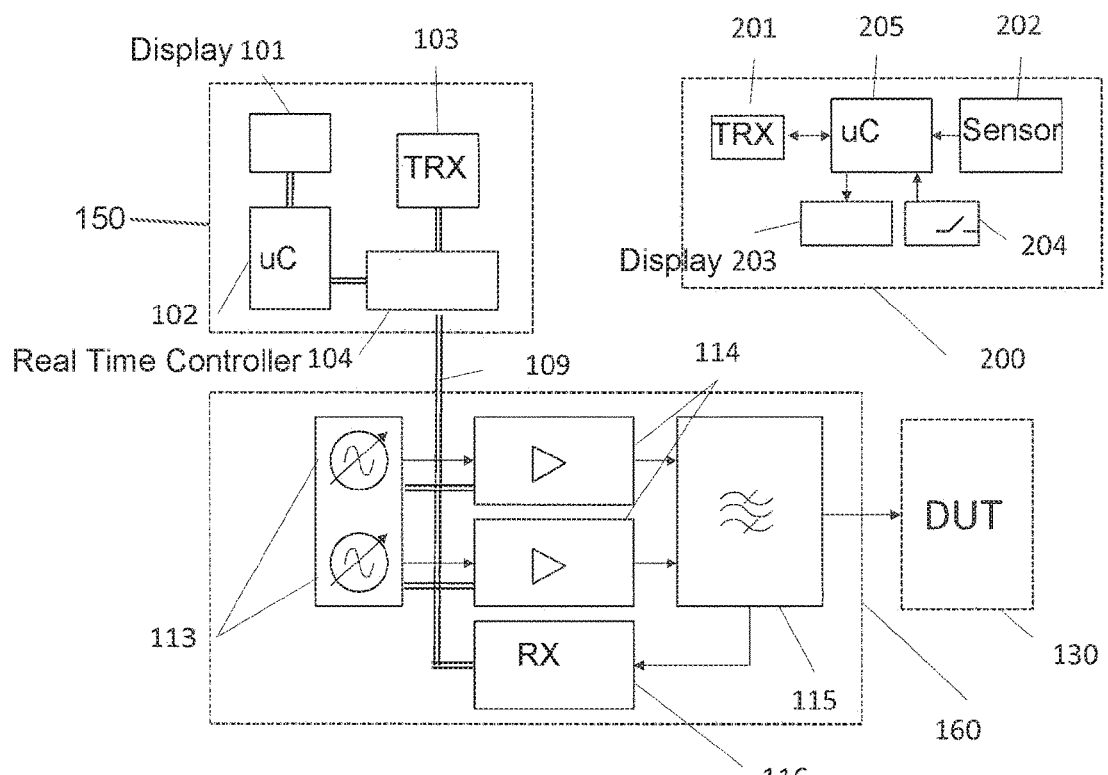
FIG. 2 is a block diagram showing in more detail the structure of the test system shown schematically in FIG. 1.

The tool with which individual points of the transmission path are tapped is designed according to the invention as a test hammer 200. The test hammer 200 contains a transmission module 201, a motion sensor 202, one or more display elements 203 (two display elements are shown in FIG. 2) and at least one button 204. The test hammer 200 and the measuring apparatus 100 are interconnected via the transmission module 201, a radio channel 300 and a transmission module 103 contained in the measuring apparatus 100.

FIG. 2 is a block diagram showing in more detail the structure of the test system shown schematically in FIG. 1.

In the test hammer 200, the transmission module 201, the motion sensor 202, the display elements 203 and the button 204 are connected to a microcontroller (μC) 205 which controls the operation of the test hammer 200.

The remotely controllable PIM analyzer 100 consists of a control unit 150 and a signal unit 160 which are interconnected by means of a signal bus 109.

In the signal unit 160, two high-frequency signals are generated with suitable different frequencies and in two signal generators 113 and are amplified in two power amplifiers 114. The two transmit signals are combined in a filter 115 and are transmitted as a test signal to the DUT 130. The PIM occurring in the DUT is selected in the filter 115 and is detected and measured as a measuring signal in a measuring receiver 116. Duplex filters which have different passbands in the transmit direction and the receive direction are conventionally used for the filter 115.

The control, the evaluation of the measurement results and their presentation are performed in the control unit 150. Said control unit contains a display 101, a computer 102 in the form of a microcontroller (μC), a transmission module 103 and a real-time controller 104. A signal bus 109 to control the signal unit 160 is connected to the real-time controller 104.

The term "real-time" refers in the context of information technology to systems that can deliver specific results reliably within a predetermined period of time. In DIN 44300, the term "real-time" is defined as " . . . operation of a computer system with programs that are at any time ready to process data in a way that the computation results are available within a given period of time." In the context of the present invention, this term relates to the fact that the real-time controller 104 must be suitable for switching or retrieving various components reliably within a predetermined short period of time to or from an energy-saving mode in response to a control signal received from an external source.

The measuring apparatus 100 has three operating modes: a measuring mode in which all units are switched on and ready for operation, a first energy-saving mode in which only the components consuming a particularly large amount of power are switched to the energy-saving mode, and a second energy-saving mode in which a further portion of the components of the measuring apparatus 100 are switched to the energy-saving mode. In particular, in the measuring apparatus 100, in the first energy-saving mode, the power amplifiers 114 are switched to the energy-saving mode, whereas, in the second energy-saving mode, the signal generators 113, the measuring receiver 116, the microcontroller 102 and the display 101 are additionally switched to the energy-saving mode. The transmission module 103 and the real-time controller 104 always remain in operation in order to be able to receive control signals from an external source and to be able to retrieve the individual components of the measuring apparatus 100 quickly from the energy-saving mode via internal control buses and the signal bus 109 in response to the control signals.

The retrieval of the power amplifiers 114 from the energy-saving mode is particularly time-critical. In order to achieve a high saving on the energy consumption, these power-intensive components are only switched on immediately before the tapping on the point under test of the device under test 130. To do this, a signal indicating the start of an impact is detected via the motion sensor 202 contained in the test hammer 200, whereupon a control signal is transmitted via the radio link to the measuring apparatus 100 and the power amplifiers 114 are switched on in response to the reception of this signal. So that a test signal can still be output to the device under test 130 before the impact of the test hammer 200, the real-time controller 104 must be able to retrieve the power amplifiers 114 from the energy-saving mode in less than 100 ms after receiving the control signal, preferably in less than 50 ms, in a further preferred manner in less than 20 ms, and in an even further preferred manner in less than 10 ms.

If the real-time controller 104 is therefore also able to switch the power amplifiers 114 to the energy-saving mode within a corresponding period of time and is also able to retrieve or switch the other components from or to the energy-saving mode in a corresponding period of time, the speed of the real-time controller 104 is of particular importance for the retrieval of power amplifiers 114 from the energy-saving mode.

A measuring cycle for measuring PIM with the test system described above is described below.

Figure 3:
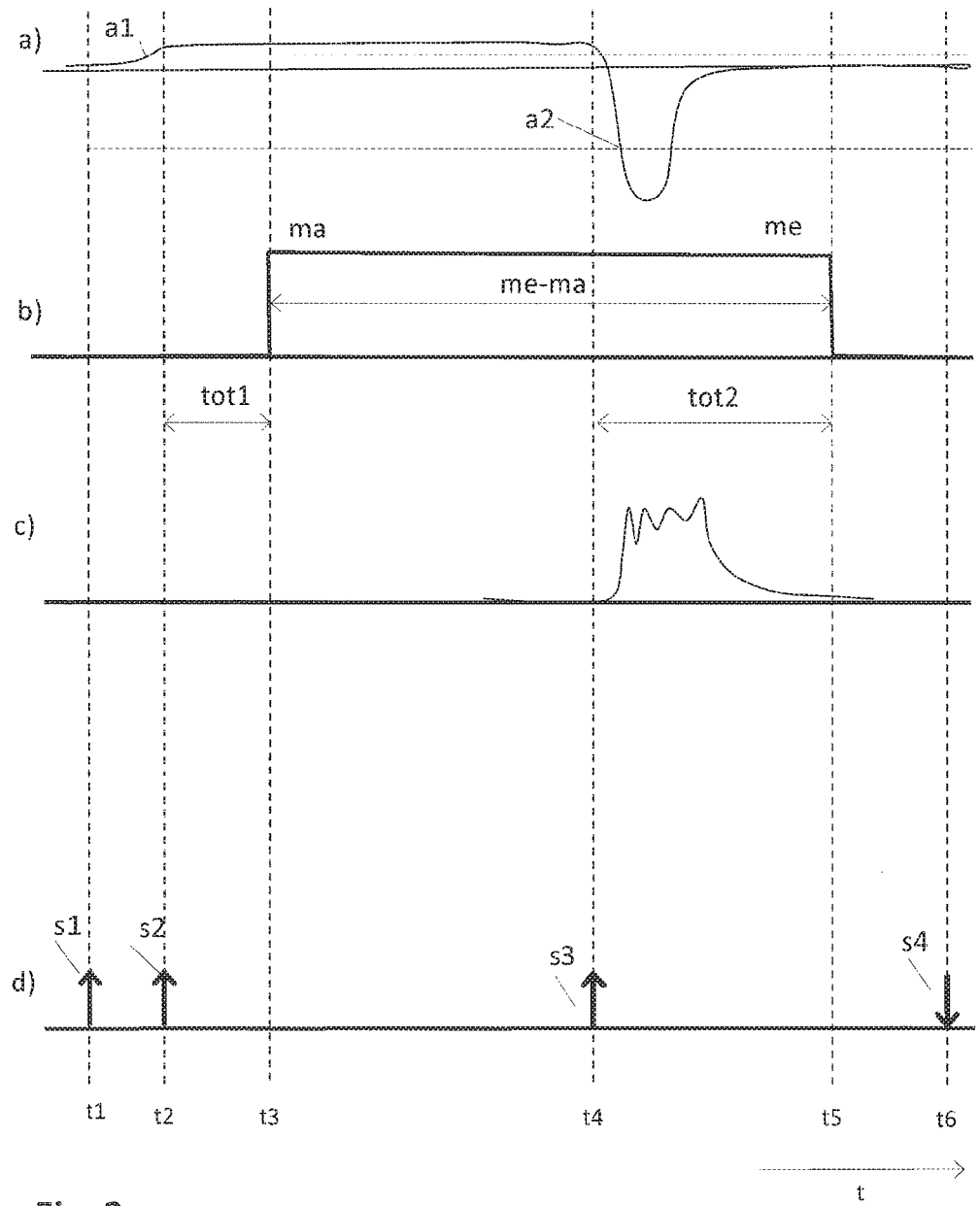
FIG. 3 is a time diagram showing a measuring cycle of the test system shown in FIG. 1 and FIG. 2.

FIG. 3 is a time diagram, not drawn to scale, showing a measuring cycle of the test system shown in FIG. 1 and FIG. 2 when an acceleration sensor is used as the motion sensor 202. The signal characteristics here show:
 a) an acceleration detected by the acceleration sensor 202,
 b) a measuring period between the start of a measuring process (ma) and the end of the measuring process (me),
 c) a level of an occurring PIM interference, and
 d) signals transmitted and received by the test hammer 202.

Along with the actual measuring process from ma to me, the measuring cycle also includes preparatory and follow-up processes.

Before the start of a measuring cycle, the measuring apparatus 100 is in the second energy-saving mode in which, besides the power amplifiers 114, further components are also switched off. The measuring apparatus 100 is permanently connected to the DUT 130 while the operator moves to the individual test points of the DUT 130, for example to the different high-frequency connectors 17 to 22 shown in FIG. 5.

When the operator has reached a test point, he actuates the button 204 to initiate a measuring cycle (time t1 in FIG. 3). At this time, a control signal s1 is transmitted by the microcontroller 205 and the transmission modules 201 and 103 to the control unit 150, indicating that the button has been actuated (button actuation indication signal). On receiving this button actuation indication signal, the real-time controller retrieves the signal generators 113, the measuring receiver 116, the microcontroller 102 and the display 101 from the energy-saving mode. These elements have a comparatively low power consumption but need a longer lead-time before the measurement begins. Thus, for example, the signal generators must supply a stable signal at the start of the measurement (ma). This state therefore corresponds to the first energy-saving mode in which only the particularly power-intensive elements such as the power amplifiers 114 remain in the energy-saving mode.

From the time t1, the microcontroller 205 contained in the test hammer measures all signals of the acceleration sensor 202. When the operator proceeds to strike the section to be tested of the DUT 130, e.g. one of the high-frequency connectors 17 to 22 shown in FIG. 5, the acceleration (speed increase) occurring when the test hammer 200 is set in motion is measured by the acceleration sensor 202 and is evaluated by the microcontroller 205. If the absolute value of the measured acceleration exceeds a predetermined first threshold a1 (time t2 in FIG. 3), a second control signal s2 is transmitted to the control unit 150, indicating that a strike with the test hammer 200 has started (strike start indication signal). By means of this second control signal s2, a timer is started in the real-time controller 104 which, after a first delay tot1 (switch-on delay), switches the power amplifiers 114 on and thus starts the measurement (time t3=t2+tot1 in FIG. 3). In contrast to the other components, such a short a lead-time before the impact of the test hammer is sufficient for the power amplifiers 114 to output the test signal in stable form to the DUT. The delay tot1 is selected here in such a way that the power amplifiers 114 are not switched on too early, in order to save energy, but also not too late, so that, on impact of the test hammer, the test signal is applied in stable form to the DUT.

When the test hammer 200 strikes the DUT 130 (time t4 in FIG. 3), a powerful acceleration (sudden speed reduction) occurs which is detected by the acceleration sensor 202 and is evaluated by the microcontroller 205. This acceleration occurring on impact of the test hammer 200 is substantially greater than the acceleration at the beginning of the strike. This impact is therefore established by comparing the absolute value of the detected acceleration with a predetermined second threshold value a2 which is greater than the first threshold value. If the measured acceleration exceeds the second threshold value a2, a third control signal s3 is transmitted to the control unit 150 indicating that an impact of the test hammer 200 has taken place (impact indication signal). By means of this impact indication signal s3, a timer is started once more in the real-time controller 104, said timer switching the power amplifiers 114 once more to the energy-saving mode after a second delay tot2 (switch-off delay) and therefore ending the measurement (time t5=t4+tot2 in FIG. 3). This corresponds to the first energy-saving mode in which the remaining units (e.g. the signal generators 113, the measuring receiver 116, the microcontroller 102 and the display 101) further remain in operation.

As shown in curve c) from FIG. 3, an increased PIM may occur between the times t4 and t5 due to the mechanical vibrations triggered by the strike on the test point. The microcontroller 102 establishes whether the measured PIM interference exceeds a predetermined threshold and outputs the result via the transmission module 103 as a result signal s4 to the test hammer 200. The PIM is preferably measured by evaluating the respective peak value of a measuring process (ma to me) (max-hold mode).

Following the transmission of the result signal s4, the microcontroller 102 switches the measuring apparatus 100 once more to the energy-saving mode (second energy-saving mode).

In the test hammer 200, the microcontroller 205 evaluates the result signal s4 and displays the result via the display elements 203.

The simplest variant of the display of the result is effected via a single display element which may, for example, be formed from a red/green light-emitting diode (LED). If the result signal s4 indicates that the PIM interference has remained below the predetermined threshold, the LED illuminates green. Conversely, if the result signal s4 indicates that the PIM interference has exceeded the predetermined threshold, the LED illuminates red. Alternatively, two separate display elements can be used, e.g. one green and one red light-emitting diode.

Figure 4:
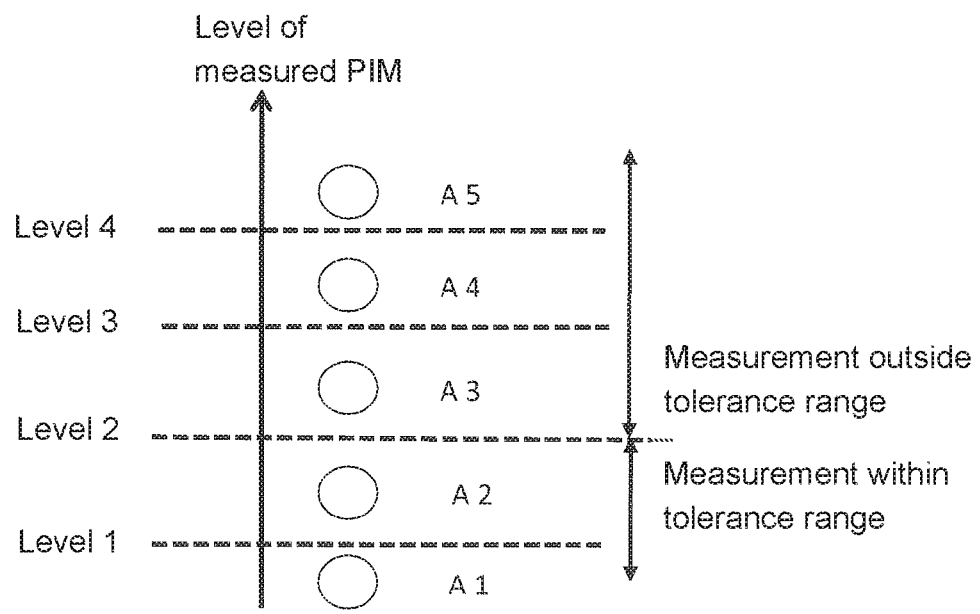
FIG. 4 is a schematic representation showing an example of a mode of operation of display elements on a test hammer shown in FIG. 1 and FIG. 2.

FIG. 4 shows a further possible arrangement of simple display elements such as e.g. LEDs which indicate a result through illumination or non-illumination, and their assignment to a result of the measurement. Here, the measured PIM is compared not only with a single threshold value, but with four threshold values having different levels (level 1 to level 4). Five display elements A1 to A5 indicate whether the measured threshold value lies below level 1, between level 1 and 2, etc., up to above level four. A value below level 2 lies within the tolerance range, which can be indicated by the display elements A1 and A2 being green LEDs or the display element A1 being a green LED and the display element A2 being an amber LED, whereas the display elements A3 to A5 are red LEDs. In principle, any given number of display elements is conceivable, their number preferably being small, for example 10 or fewer, in a further preferred manner 5 or fewer.

As a further alternative, light bars, digital displays or similar display elements with which measurement results are normally presented can obviously also be used.

The parameters of the measuring apparatus 100 necessary for the measurement, e.g. the delays tot1 and tot2 and the levels of the threshold values with which the measured PIM is compared, can be set via software in the measuring apparatus 100.

The parameters of the test hammer 200, e.g. the threshold values a1 and a2 with which the measured acceleration is compared, can be modified via input elements (e.g. a keyboard) on the measuring apparatus 100 and can then be transmitted via the radio link 300 to the remote control.

In the embodiment described, each measuring cycle is started by pressing the button 204. Alternatively, the measuring apparatus can also be switched once more to the energy-saving mode, not directly following the transmission of the result signal s4, but only after a further delay if a control signal s2 has not been received in the meantime. The operator can thus perform a plurality of test processes in succession without having to actuate the button 204 each time. The measuring apparatus 100 then switches to the energy-saving mode only after a longer pause. Only the power-intensive components (in the embodiment described the power amplifiers 114) are switched to the energy-saving mode at the end of each measuring process (me). In a further alternative, one or more further buttons are provided on the test hammer, with which the operator can specify how many strikes he carries out with the test hammer before the measuring apparatus switches once more to the second energy-saving mode. In a further alternative, no button 204 at all is provided on the test hammer, so that only the first energy-saving mode is then implemented, in which only the power-intensive components are switched to the energy-saving mode at the end of each measuring process.

Alternatively or additionally to the quantity of the acceleration, the direction of the acceleration can also be detected. Thus, the acceleration on impact has a different direction to that at the beginning of the strike. Even if the two directions do not have to be directly opposite (angle) 180° due to a possible rotation of the test hammer during the strike, the acceleration on impact nevertheless has an adequately large component in a direction opposite to the direction as the start of the strike.

The motion sensor is implemented in the described embodiment by means of an acceleration sensor. However, the start of the strike or impact of the test hammer can also be detected in a different manner. Thus, for example, the distance between the test hammer and the DUT can be measured with a distance sensor, such as e.g. a capacitive distance sensor, and the start of the strike or impact of the test hammer can be detected from a change in the distance over time. Inclination or position sensors can also be used.

Even if two high-frequency signals are used as a test signal in the embodiment described, the invention is not restricted thereto. The test signal can also be formed from only a single signal or from more than two signals.

Nor is the present invention limited to PIM measurement, but can be used in any measuring method in which a measurable result is produced by means of mechanical vibration of a test point, indicating whether or not the test point meets a predetermined quality criterion.

What is claimed is:

1. A test hammer for testing a test object, the test hammer making a strike on the test object, the test hammer comprising:
   an acceleration sensor; and
   wherein the test hammer outputs
   a strike-start indication signal when the acceleration sensor detects a first motion state by detecting a first acceleration exceeding a predetermined first threshold, the first motion state indicating a start of the strike, and
   an impact indication signal when the acceleration sensor detects a second motion state by detecting a second acceleration which exceeds a predetermined second threshold or by detecting a third acceleration having a directional component opposite to a direction of the first acceleration which has exceeded the predetermined first threshold, the second motion state indicating an impact of the test hammer.

2. The test hammer as claimed in claim 1,
   further comprising a button,
   wherein the test hammer outputs a button-actuation indication signal if the button has been actuated.

3. The test hammer as claimed in claim 1,
   further comprising a display;
   wherein the test hammer receives a result signal, and the test hammer presents a result conveyed by the result signal on the display.

4. The test hammer as claimed in claim 3,
   wherein the display comprises light-emitting display elements which illuminate or do not illuminate depending on the result signal, or
   wherein the display comprises a single light-emitting display element that illuminates in different colors depending on the result signal.

5. The test hammer as claimed in claim 4, wherein the display element is a light emitting diode.

6. A test system for testing a test object, the test system comprising:
   a test hammer for making a strike on the test object, the test hammer comprising
   an acceleration sensor; and
   wherein the test hammer outputs
   a strike-start indication signal once the acceleration sensor detects, by detecting a first acceleration exceeding a predetermined first threshold, a first motion state that indicates a start of the strike, and
   an impact indication signal once the acceleration sensor detects, by detecting a second acceleration which exceeds a predetermined second threshold or by detecting a third acceleration having a directional component opposite to a direction of the first acceleration which has exceeded the predetermined first threshold, a second motion state that indicates an impact of the test hammer; and
   wherein the test system further comprises a measuring apparatus for measuring a test property of the test object, the measuring apparatus comprising
   a plurality of functional units,
   the measuring apparatus generating a test signal;
   the measuring apparatus outputting the test signal to the object being tested;
   the measuring apparatus for receiving a measuring signal, the measuring signal being produced in response to the output of the test signal;
   the measuring apparatus determining a quantity of a component of the measuring signal corresponding to the test property being measured; and
   the measuring apparatus receiving a control signal from an external source; and
   wherein the measuring apparatus further comprises a real-time controller,
   the real-time controller switching at least a first functional unit from the plurality of functional units from a normal mode to an energy-saving mode in a predetermined time in response to the control signal received from the external source or
   the real-time controller switching at least a first functional unit from the energy-saving mode to the normal mode in the predetermined time in response to the control signal received from the external source.

7. The test system as claimed in claim 6, wherein the real-time controller
   retrieves a second functional unit of the plurality of functional units from the energy-saving mode in response to the strike-start indication signal received from the test hammer, a power consumption of the second functional unit being greater than a power consumption of the first functional unit; or
   switches the second functional unit being to the energy-saving mode in response to the impact indication signal received from the test hammer; or switches the first functional unit to the energy-saving mode subsequent to a completion of a determination of a quantity of a component of the measuring signal corresponding to the property to be measured of the test object under test.

8. The test system as claimed in claim 7, further comprising a timer generating a first delay and a second delay,
wherein the real-time controller retrieves the second functional unit from the energy-saving mode in response to the strike-start indication signal received from the test hammer delayed by the first delay, or
wherein the real-time controller switches the second functional unit to the energy-saving mode in response to the impact indication signal received from the test hammer delayed by the second delay.

9. The test system as claimed in claim 6, wherein the predetermined time is 100 ms or less.

10. The test system as claimed in claim 6,
wherein the test property is a non-linearity;
wherein the test signal comprises two high-frequency signals having different frequencies;
wherein the measuring signal comprises signal components produced by passive intermodulation, and
wherein the measuring apparatus further determines whether a signal component produced by passive intermodulation exceeds a predetermined threshold.

11. The test system as claimed in claim 6, wherein
the test hammer further comprises a button,
the test hammer outputs a button actuation indication signal if the button has been actuated, and
the measuring apparatus retrieves a first functional unit from the energy-saving mode in response to the button actuation indication signal received from the test hammer.

12. A method for measuring a property of a test object using a test system,
the test system comprising
a test hammer for making a strike on the test object, the test hammer comprising
a acceleration sensor;
the test hammer outputting,
a strike-start indication signal once the acceleration sensor detects a first motion state that indicates a start of the strike by detecting a first acceleration exceeding a predetermined first threshold, and
an impact indication signal once the acceleration sensor detects a second motion state that indicates an impact of the test hammer by detecting a second acceleration which exceeds a predetermined second threshold or by detecting a third acceleration having a directional component opposite to a direction of the first acceleration which has exceeded the predetermined first threshold; and
the test system further comprising a measuring apparatus for measuring a test property of the test object,
the measuring apparatus comprising a plurality of functional units:
the measuring apparatus generating a test signal;
the measuring apparatus outputting the test signal to the object being tested;
the measuring apparatus receiving a measuring signal, the measuring signal being produced in response to the output of the test signal;
the measuring apparatus determining a quantity of a component of the measuring signal corresponding to the test property being measured; and
the measuring apparatus receiving a control signal from an external source; and
wherein the measuring apparatus comprises a real-time controller, the real-time controller places at least a first functional unit in an energy-saving mode in a predetermined time in response to a control signal received from an external source or
the real-time controller switching at least a first functional unit from the energy-saving mode to the normal mode in the predetermined time in response to the control signal received from the external source;
the method comprising the steps of:
(a) connecting the measuring apparatus to the test object;
(b) striking the test object with the test hammer; and
(c) determining, by the measuring apparatus, the quantity of the component of the measuring signal corresponding to the property to be measured.

13. The method as claimed in claim 12, further comprising the following steps between step (a) and step (b)
actuating a button on the test hammer;
outputting, from the test hammer, a button actuation indication signal in response to the actuation of the button; and
switching, by the real-time controller, the at least one functional unit from the energy-saving mode to a normal mode in the predetermined time in response to the button actuation signal received from the test hammer.

14. The method as claimed in claim 12, wherein step (b) further comprises
(b1) detecting, with the acceleration sensor, the first motion state, the first motion state indicating the start of the strike;
(b2) outputting, from the test hammer, the strike-start indication signal when the acceleration sensor detects the first motion state, and
(b3) switching, by the real-time controller, a second functional unit of the plurality of functional units from the energy-saving mode to a normal mode in response to the control signal received from the test hammer, wherein the control signal comprises the strike-start indication signal.

15. The method as claimed in claim 14, wherein step (b3) further comprises generating a first delay, and
delaying switching the second functional unit from the energy-saving mode to the normal mode by the first delay after receiving the strike-start indication signal.

16. The method as claimed in claim 12, wherein step (b) comprises
(b4) detecting, with the acceleration sensor, the second motion state, the second motion state indicating the impact of the test hammer;
(b5) outputting, from the test hammer, the impact indication signal when the acceleration sensor detects the second motion state; and
(b6) switching, the real-time controller, a second functional unit of the plurality of functional units from a normal mode to the energy-saving mode in response to the control signal, wherein the control signal received from the test hammer comprises the impact indication signal.

17. The method as claimed in claim 16, wherein step (b6) comprises
   generating a second delay time, and
   delaying switching the second functional unit from the normal mode to the energy-saving mode by the second delay time after receiving the impact indication signal.

18. The method as claimed in claim 12, wherein step (b) comprises
   determining whether a component of the measuring signal corresponding to the property to be measured of the test object under test exceeds a predetermined threshold,
   outputting, by the measuring apparatus, a result of the determination as a result signal,
   switching, by the real-time controller, the at least one functional unit from a normal mode to an energy saving mode in the predetermined time in response to the control signal received from the external source, wherein the control signal comprises the result signal, and
   displaying the result of the determination on the display of the test hammer based on the result signal received from the measuring apparatus.

* * * * *